United States Patent [19]
Elting et al.

[11] Patent Number: 5,200,316
[45] Date of Patent: Apr. 6, 1993

[54] IMMUNOASSAY METHODS USING NONCROSS REACTIVE CEA GENE FAMILY MEMBERS ANTIBODIES

[75] Inventors: James Elting, Madison; Thomas Barnett, Prospect; Michael Kamarck, Bethany; John Hart, Wallingford, all of Conn.

[73] Assignee: Miles Inc., Elkhart, Ind.

[21] Appl. No.: 480,428

[22] Filed: Feb. 15, 1990

[51] Int. Cl.$^5$ .................... G01N 33/574; C12Q 1/68
[52] U.S. Cl. ........................................ 435/6; 435/7.2; 435/7.21; 435/7.23; 435/7.92; 435/973; 435/975; 436/548; 436/64; 436/813; 530/387.7; 530/388.8; 530/388.85
[58] Field of Search ............... 435/7.2, 7.21, 7.23, 435/7.92, 973, 975, 6; 436/548, 64, 813; 530/387, 387.7, 388.8, 388.85, 389.7

[56] References Cited

U.S. PATENT DOCUMENTS

| | | | |
|---|---|---|---|
| 4,467,031 | 8/1984 | Gallati et al. | 435/7 |
| 4,489,167 | 12/1984 | Ochi et al. | 436/518 |
| 4,818,709 | 4/1989 | Primus et al. | 436/518 |
| 4,871,834 | 10/1989 | Matsuoka et al. | 530/387 |
| 5,122,599 | 6/1992 | Barnett et al. | 536/27 |

FOREIGN PATENT DOCUMENTS

| | | |
|---|---|---|
| 0098162 | 6/1983 | European Pat. Off. . |
| 0263933 | 8/1987 | European Pat. Off. . |
| 0346710 | 6/1989 | European Pat. Off. . |
| 8402983 | 8/1984 | World Int. Prop. O. . |

OTHER PUBLICATIONS

Kamarck, M. E., et al., *Proc. Natl. Acad. Sci.*, USA, vol. 84, pp. 5350–5354 (1987).
Barnett, T., et al., *Genomics*, vol. 3, pp. 59–66, (1988).
Radosevich, J. A., et al., Biological Abstracts, vol. 89, No. 6, the abstract No. 60880 (1989).
Suzuki, N., et al., Biological Abstracts, vol. 84, No. 11, the abstract No. 109915 (1987).
Kitagawa, H., et al., Biological Abstracts, vol. 83, No. 1, the abstract No. 5454 (1987).
Buchegger, F., et al., Biological Abstracts, vol. 78, No. 9, the abstract No. 68827 (1984).
The Journal of Cell Biology, vol. 108, No. 2, Feb. 1989, pp. 267–276.
Thomas R. Barnett et al. "Carcinoembryonic Antigens: Alternative Splicing Accounts for the Multiple mRNAs that Code for Novel Members of the Carcinoembryonic Antigen Family".
Critical Reviews in Oncology/Hematology, vol. 2, issue 4, 1985, pp. 355–396, John E. Shively et al., "CEA–Related Antigens: Molecular Biology and Clinical Significance".

*Primary Examiner*—Esther L. Kepplinger
*Assistant Examiner*—Toni R. Scheiner
*Attorney, Agent, or Firm*—Andrew L. Klawitter

[57] ABSTRACT

Immunoassay methods useful for the determination of the presence or absence of CEA gene family members are provided. Methods are provided that differentiate between members of the CEA gene family. In addition, monoclonal antibodies against CEA-family members, said antibodies specific to TM-CEA, CEA, or NCA, and not cross-reactive with other CEA family members are provided. Further, antibodies specific to two of three CEA gene family member, TM-CEA and NCA but not CEA and CEA and NCA but not TM-CEA, TM-CEA and CEA but not NCA, are provided. Said monoclonal antibodies include antibodies against native protein and antibodies against denatured protein. Also provided are hybridoma cell lines secreting said antibodies, and pharmaceutical compositions containing said antibodies or fragments thereof.

13 Claims, 9 Drawing Sheets

IMMUNOASSAY METHODS USING NONCROSS REACTIVE CEA GENE FAMILY MEMBERS ANTIBODIES

BACKGROUND OF THE INVENTION

A major problem in determining the tumor-specificity and clinical applications of carcinoembryonic antigen (CEA) is the close homology with other glycoproteins of the CEA gene family which are expressed by tumors. CEA is a glycoprotein with molecular weight of approximately 180 kD that is one of a family of genes that encode approximately 8-10 highly similar proteins. CEA has been used as a serum marker for tumors of the colon, breast, and lung. The high degree of structural and sequence similarity between members of the CEA gene family explains the immunological cross-reactivity seen among existing immunological reagents. (See Shively et al, 1985. CEA-related antigens: Molecular biology and clinical significance. CRC Crit. Rev. Oncol. Hematol. 2:355-399; Barnett et al, 1989. Carcinoembryonic antigens: Alternative splicing accounts for the multiple mRNAs that code for novel members of the carcinoembryonic antigen family. J. Cell Biol. 108:267-276.)

Two CEA family members which share epitopes with CEA are Normal Cross Reacting Antigen (NCA) and a set of proteins that contain membrane spanning and cytoplasmic domains called transmembrane-CEA (TM-CEA). We have isolated and sequenced the complete cDNAs coding for CEA, NCA, and multiple transcripts of TM-CEA and have produced transfectant cell lines which express these CDNAS. These are the subject matter of co-pending applications U.S. application Ser. Nos. U.S. Pat. No. 5,122,599, 231,741, and 249,922 and articles. Barnett et al suora; Barnett et al. 1988. Carcinoembryonic antigen family: characterization of cDNAs coding for NCA and CEA and suggestion of non-random sequence variation in their conserved loop domains. Genomics. 3:59-66; Kamarck et al, 1987. Carcinoembryonic antigen family: Expression in a mouse L-cell transfectant and characterization of a partial cDNA in bacteriophage lambda gt11. Proc. Natl. Acad. Sci. U.S.A. 84:5350-5354. "Transfectant murine cell lines that express TM-CEA, NCA, and CEA, as described in U.S. patent application Ser. No. 249,922, have been deposited with the American Type Culture Collection (ATCC), Rockville, Md., U.S.A. ATCC 9731, 9732, and 9733, deposited Jun. 1, 1988, express TM-CEA, NCA, and CEA, respectivley." Antibodies specific to CEA family member proteins would allow better and more sensitive assessment of the differential expression in various disease states.

U.S. Pat. No. 4,467,031, entitled "Enzyme-Immunoassay for Carcinoembryonic Antigen" relates to a sandwich enzyme immunoassay for CEA in which the first of two anti-CEA monoclonal antibodies is attached to a solid phase and the second monoclonal is conjugated with peroxidase.

U.S. Pat. No. 4,489,167, entitled "Methods and Compositions for Cancer Detection", describes that CEA shares an antigenic determinant with alpha-acid glycoprotein (AG), which is a normal component of human serum. The method described therein concerns a solid-phase sandwich enzyme immunoassay using as one antibody an antibody recognizing AG and another antibody recognizing CEA, but not AG.

EP 83303759, entitled "Monoclonal Antibodies Specific to Carcinoembryonic Antigen," relates to the production of "CEA specific" monoclonal antibodies and their use in immunoassay.

WO 84/02983, entitled "Specific CEA-family Antigens, Antibodies Specific Thereto and Their Methods of Use", is directed to the use of monoclonal antibodies to CEA-meconium (MA)-, and NCA-specific epitopes in immunoassays designed to selectively measure each of these individual components in a sample.

U.S. Pat. No. 4,818,709, entitled "CEA-family antigens, Anti-CEA antibodies and CEA immunoassay" describes antibodies specific to specific CEA epitopes and epitopes of CEA-cross-reactive antigens.

The references of the prior art do not disclose a method and reagents that can discriminate between CEA, NCA and TM-CEA gene family member proteins.

SUMMARY OF THE INVENTION

The measurement of CEA in the serum of cancer patients provides useful information to the clinician for patient management. A limitation of the use of CEA as a tumor marker is its lack of sensitivity and/or specificity. Our results have demonstrated that tumors may express more than one member of the CEA gene family. Due to the fact that multiple family members may be expressed, the generation of antibodies specific for different members of the CEA-antigen family has value for use in diagnostic and therapeutic applications. Diagnostic applications include the screening of cancer patients for circulating antigens found in serum or plasma and the use of monoclonal antibodies which bind to the surface of tumor cells for tumor imaging.

Monoclonal antibodies which bind or adhere to the native cell surface antigens, protein in its native confirmation, found at the surface of tumor cells, have application in tumor imaging, as well as their use as potential therapeutics. The specificity of the antibodies to native antigens refers to their ability to bind to antigens expressed at the surface of live cells or to both antigens that are secreted by cells. The specificity of antibodies to denatured antigens refers to their ability to bind to denatured or unfolded antigens. Such antibodies have application for in vivo and in vitro studies that would allow for differentiation between antigens that would otherwise not be distinguishable because of structural similarities in their native state, i.e. conformational.

The present invention relates to an immunoassay method for differentiating between family members of the CEA gene family, said method comprising the steps of (a) contacting a source of serum or plasma in a sample with an antibody specific to one of said CEA gene family members, said antibody not cross-reactive with others of said CEA gene family members, under conditions sufficient to allow said specific antibody to bind to said specific CEA family member to form an antibody-antigen product, and (b) detecting said antibody antigen product of step (a).

The above described method may include antibodies selected from the group consisting of antibodies which (a) specifically bind to transmembrane-carcinoembryonic antigens (TM-CEA) but do not specifically bind to carcinoembryonic antigen (CEA) or normal cross reacting antigen (NCA); (b) specifically bind to CE but do not specifically bind to TM-CEA or NCA; (c) specifically bind to NCA but do not specifically bind to CEA or TM-CEA; (d) specifically bind to NCA and CEA but do not specifically bind to TM-CEA, and (e) specifically bind to TM-CEA and NCA but do not specifically bind to CEA, and (f) specifically bind to CEA and TM-CEA but do not specifically bind to NCA.

The present invention relates to the detection of CEA gene family members CEA, NCA and TM-CEA, wherein said CEA family members are the native proteins or denatured forms of the proteins.

It is also recognized that the above method could include at least two different antibodies, in a panel-like assay, which bind to at least two different CEA family members in said sample. Such a panel assay could include at least one cross-reactive antibody, cross-reactive with all CEA family members.

The antibodies of the present invention have been shown to be reactive with native and denatured CEA gene family members, as summarized in Table 1.

TABLE 1

Reactivity of MoAbs with native and denatured CEA gene family members.

| TM-CEA | NCA | CEA |
| --- | --- | --- |
| + | − | − |
| − | − | + |
| − | + | + |
| + | + | − |
| + | − | + |
| + | + | + |
| TM-CEA$^d$ | NCA$^d$ | CEA$^d$ |
| − | + | − |
| + | − | − |
| − | − | + |

$^d$ — denotes denatured protein
+ — denotes reactivity
− — denotes reactivity not detected

DETAILED DESCRIPTION OF THE INVENTION

Figure 1A:
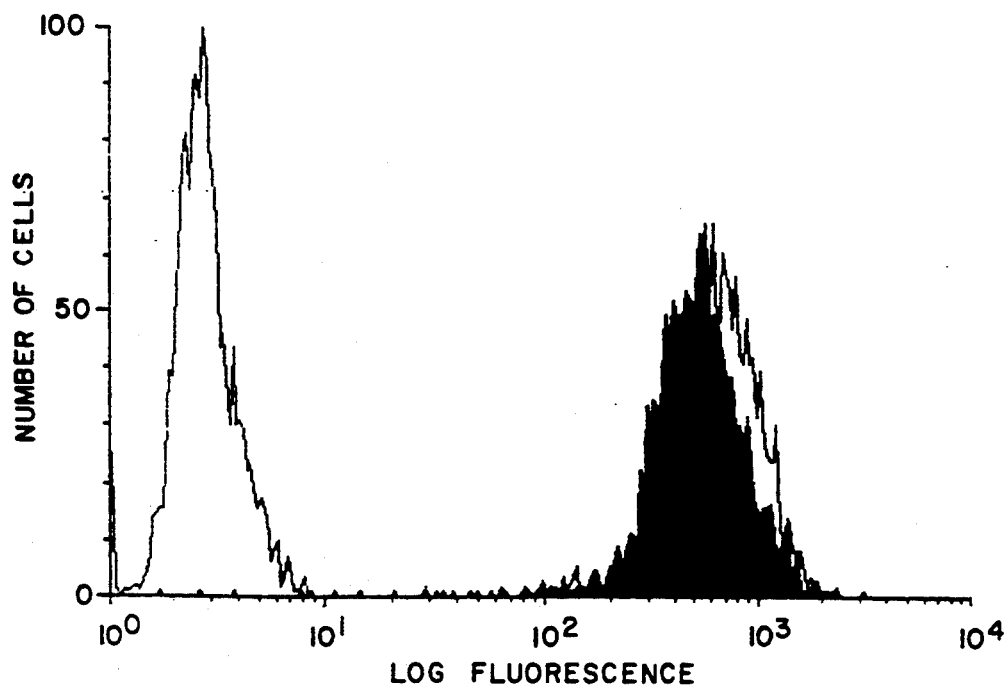
FIGS. 1A, 1B, 1C, 1D, 1E and 1F are FACS analyses demonstrating specificity of MoAb 176.7.5A.

A plurality of specific, non cross-reactive and partially cross-reactive antibodies have been generated to differentiate between CEA gene family members, TM-CEA, NCA and CEA, native or denatured. Antibodies generally include antibodies selected from the group consisting of antibodies which:

(a) specifically bind to transmembrane-carcinoembryonic antigens (TM-CEA) but do not specifically bind to carcinoembryonic antigen (CEA) or normal cross reacting antigen (NCA); (b) specifically bind to CEA but do not specifically bind to TM-CEA or NCA; (c) specifically bind to NCA but do not specifically bind to CEA o TM-CEA; (d) specifically bind to NCA and CEA but do not specifically bind to TM-CEA; (e) specifically bind to TM-CEA and NCA but do not specifically bind to CE and (f) specifically bind to CEA and TM-CEA but do not specifically bind to NCA.

Examples of monoclonal antibodies specific to native TM-CEA which are not cross-reactive with CEA or NCA include MoAb 176.7.3A, 176.7.4A and 176.7.5A.

Examples of monoclonal antibodies specific to native CEA which are not cross-reactive with TM-CEA or NCA include MoAbs 46.1, 53.4, 46.5 and 69.2. MoAbs 46.1 and 53. have demonstrated greater binding affinity to cell surfaces than MoAbs 46.5 and 69.2.

Examples of monoclonal antibodies cross-reactive to denatured NCA which are not cross-reactive with CEA and TM-CEA, native or denatured, include MoAbs against the immunogen (PSKANY)$_X$-KLH where X=2-5 repeating units.

Examples of monoclonal antibodies specific to native TM-CEA and NCA but not cross-reactive with CEA include MoAB 176.4G2.

Examples of monoclonal antibodies specific to native CEA and NCA but not cross reactive to TM-CEA include MoAb 46.4.

Examples of monoclonal antibodies specific to denatured CEA and not native protein which are not cross-reactive with TM-CEA or NCA include MoAb 119.9.

Examples of monoclonal antibodies specific to denatured TM-CEA and not native protein which are not cross-reactive with CEA or NCA include MoAb 130.10.

Examples of monoclonal antibodies cross-reactive to both CEA and TM-CEA, include MoAbs 53.5, 46.2, and 176.3G2. Representative examples of monoclonal antibodies of the present invention can be prepared as follows:

For the preparation of the antigen TM-CEA, reference is made to U.S. patent application Ser. No. 231,741 and U.S. Pat. No. 5,122,599, incorporated herein by reference.

A genomic DNA-mediated gene transfectant cell line, 23.411 Serial NO. 249,922, which has increased levels of TM-CEA at the cell surface was used as the source of antigen.

Whole cell lysates in TX-100 of 23.411 cells were first absorbed to Wheat Germ Agglutinin (WGA) bound to Separose-6MB beads. Bound glycoproteins were eluted off with 0.3M of the competing sugar N-Acetyl-D-Glucosamine. WGA eluates were then absorbed to MoAb 53.5 bound to agarose beads which recognizes both CEA and TM-CEA antigens but not NCA. The bound TM-CEA antigens were then eluted off with 50 mM NaCitrate, 1% TX-100 pH 2.5 and the eluate neutralized with 0.14 vols. of IM tris-base to keep the antigens in native conformation. Pooled aliquots of antigens were then reabsorbed to WGA sepharose, washed and eluted off in the presence of 0.5% Na-deoxycholate detergent. The eluted antigens were then dialyzed to remove the detergent prior to preparing the aqueous antigen for immunization.

Antigen was prepared for immunization by making a 1:1 emulsion of aqueous antigen in Freunds complete adjutant. A Four tenths 0.4) ml of emulsion was injected, intraperitoneally, to each of 5 Balb/c mice. Five boost immunizations were done at two week intervals with 0.4 ml of the 1:1 emulsion of aqueous antigen in Freunds incomplete adjutant. Serum taken from mice seven days after immunization showed greater reactivity to 23.411 cells as compared to mouse control cell line LTK-A. Spleens were removed 10 days after the last boost and fused to myeloma cells P3-X63-AG8.653 using standard fusion protocols. (Kearney, J. F., Radbrunch, A., Liesegang, B. and Rajewsky, 1979. A new myeloma cell line that has lost immunoglobulin expression but permits the construction of antibody secreted hybrid cell lines. J. Immuno 1.123:1548-1550).

The transfectant cell line 23.411 was used for screening hybridoma supernatants for antibodies binding to native cell surface antigens. Viable cells were stained by indirect immunofluorescence (IIF) using individual hybridoma supernatants as first antibody with subsequent analysis on a Fluorescence Activated Cell Sorter (FACS). Hybridoma supernatants showing binding to 23.411 cells were subsequently rescreened against the transfectant cell panel containing mouse L cell transfectants which specifically express CEA and NCA. A determination of antigen specificity was made for each MoAb.

An immunization protocol using whole 23.411 cells for immunizing antigens resulted in the production one hybridoma making an Ab of $I_gM$ subtype that was cross-reactive to all CEA family members.

Three fusions were performed with spleens from mice immunized with purified antigens resulted in three hybridomas of interest. Fusions 157 and 158 resulted in 650 clones, one hundred and fourteen were positive against 23.411. Twenty of the 114 were subcloned further after transfectant cell panel screenings. Six of the twenty were further subcloned, resulting in one MoAb C158.7 which demonstrated specificity for TM-CEA but very poor affinity. An additional fusion, 176, resulted in 360 clones, thirty of which were positive against 23.411. Fourteen of the 30 were subcloned further resulting in four MoAbs C176.7.1A, C176.7.5A, C176.3G2 and C176.4G2. MoAbs C176.7.1A and C176.3G2 were determined to be identical. The antibodies were all of IgG-1 subtype.

As a result of the above screening process, three monoclonal antibodies, of interest were isolated. MoAb 176.7.5A shows cell surface binding specificity for TM-CEA but not for CEA or NCA as expressed on 3 different transfectant cell lines 23.411, E22.7 and C16.6. A second antibody, 176.4G2 showed specificity for TM-CEA and NCA but not CEA.

Figure 1B:
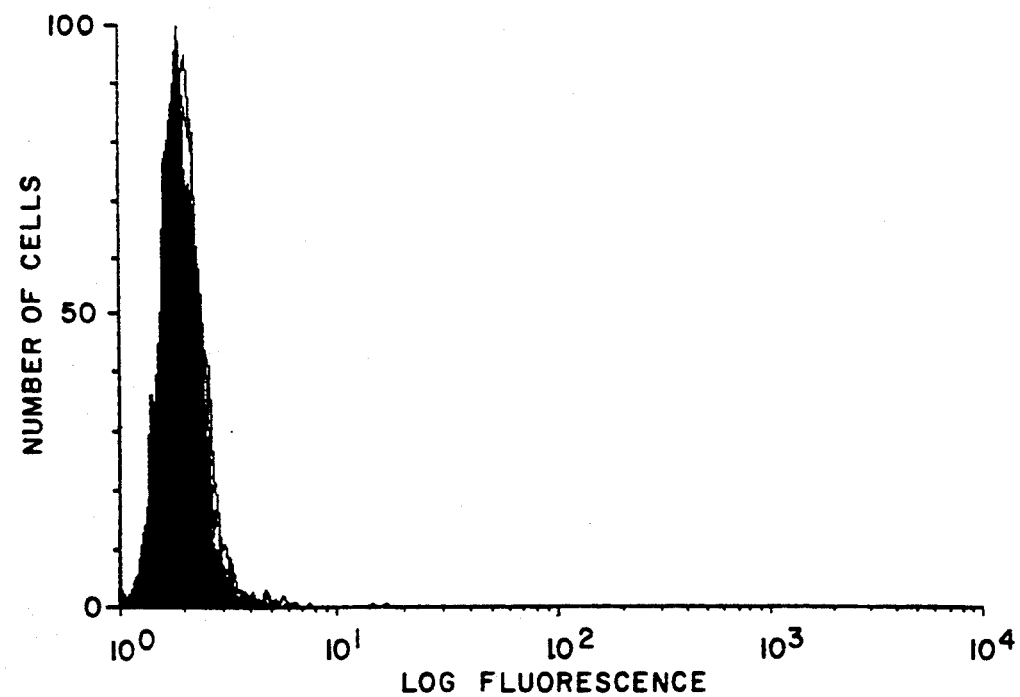
Figure 1C:
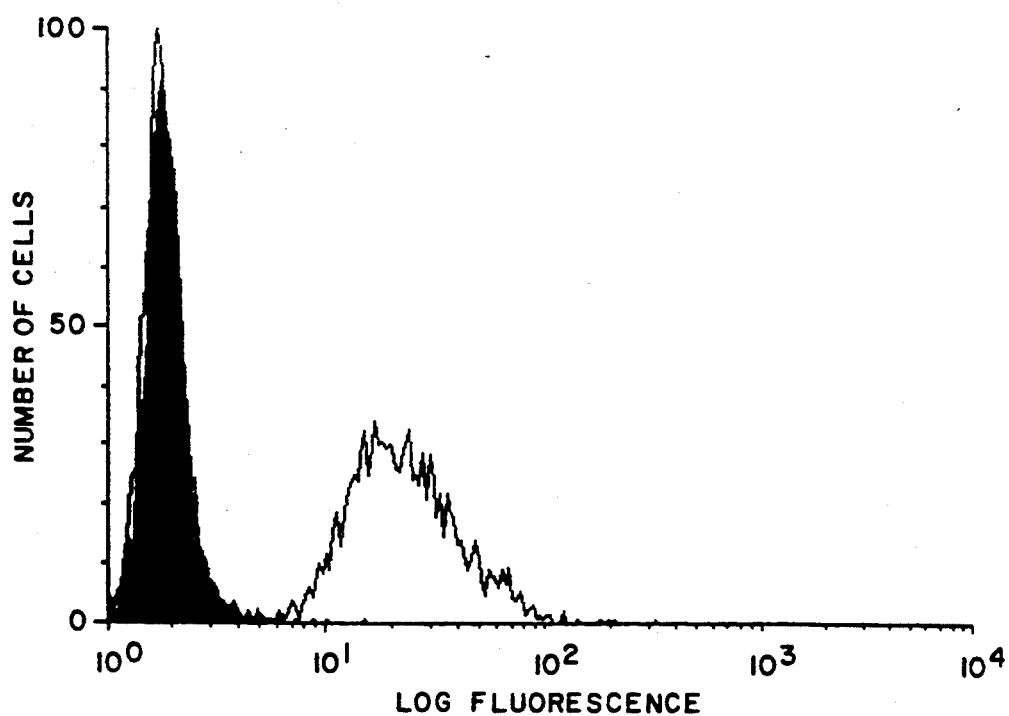
Figure 1D:
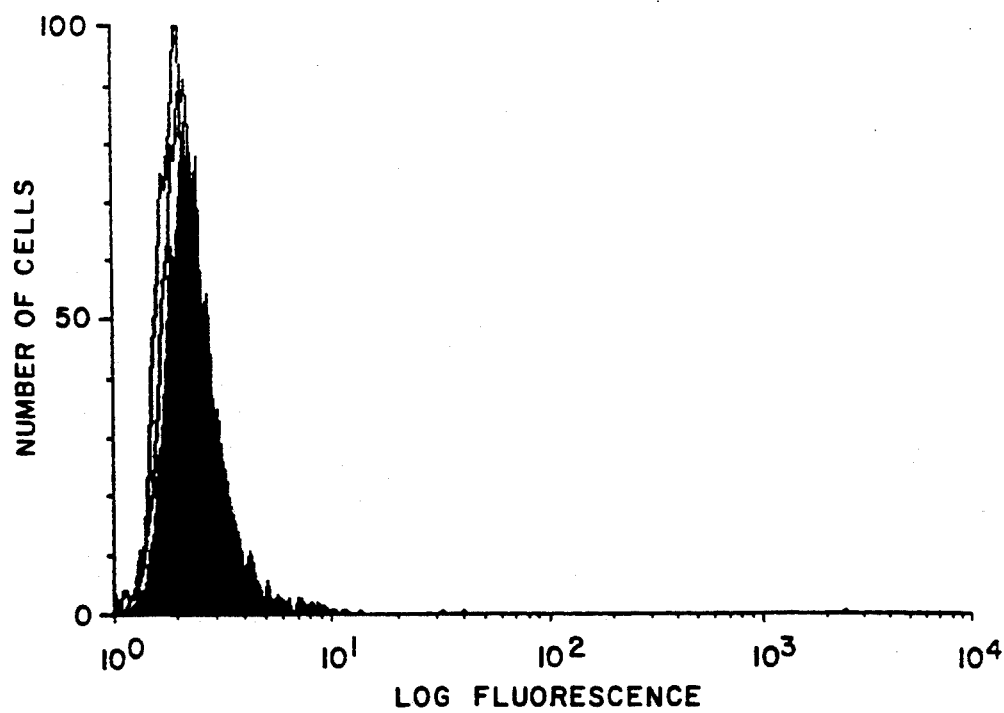
Figure 1E:
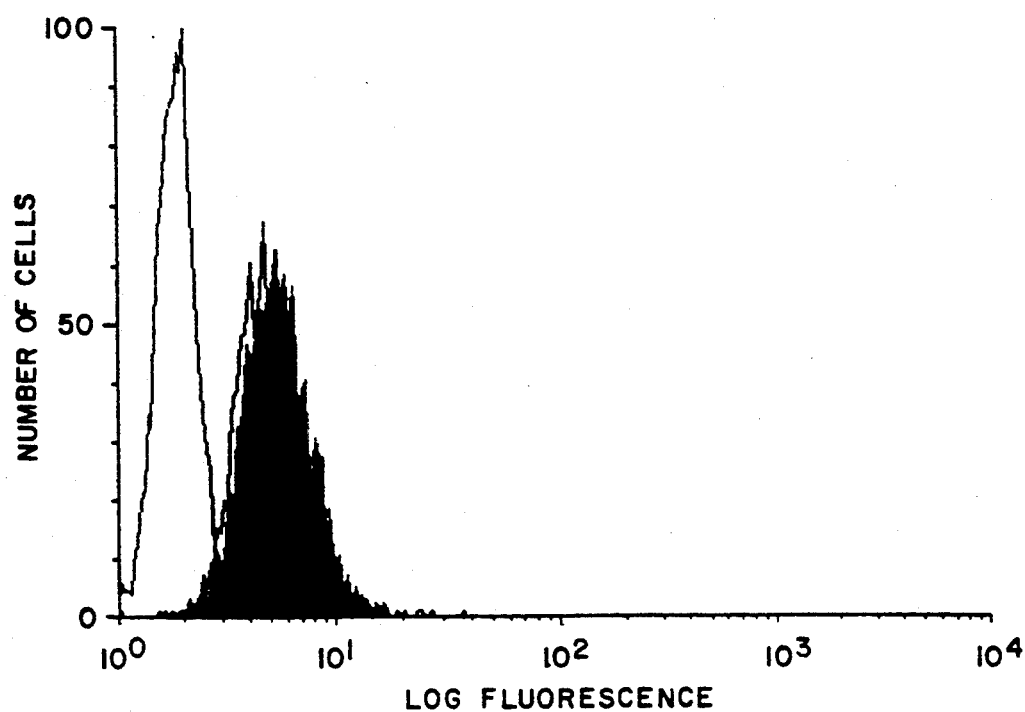
Figure 1F:
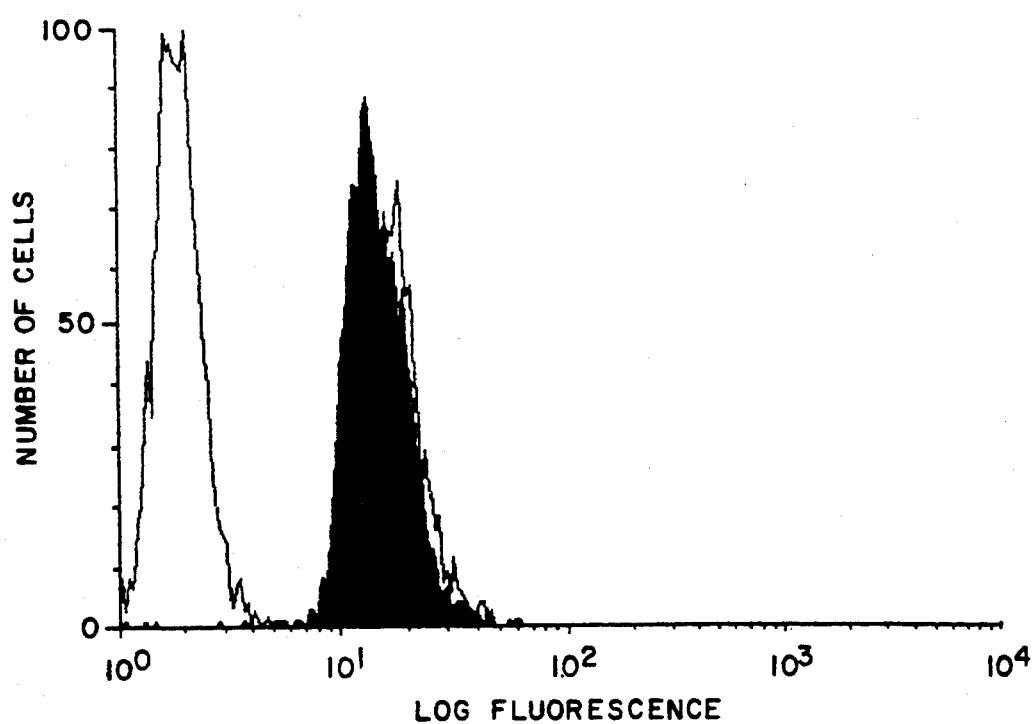
Figure 2A:
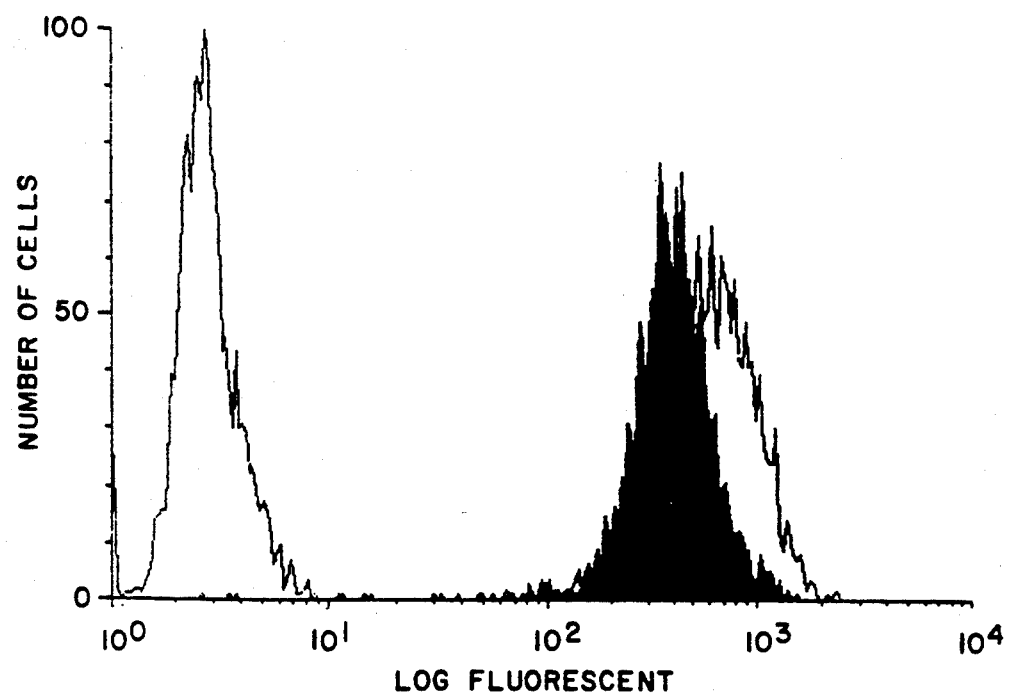
FIGS. 2A, 2B, 2C, 2D, 2E and 2F are FACS analyses demonstrating specificity of MoAb 176.3G2.
Figure 2B:
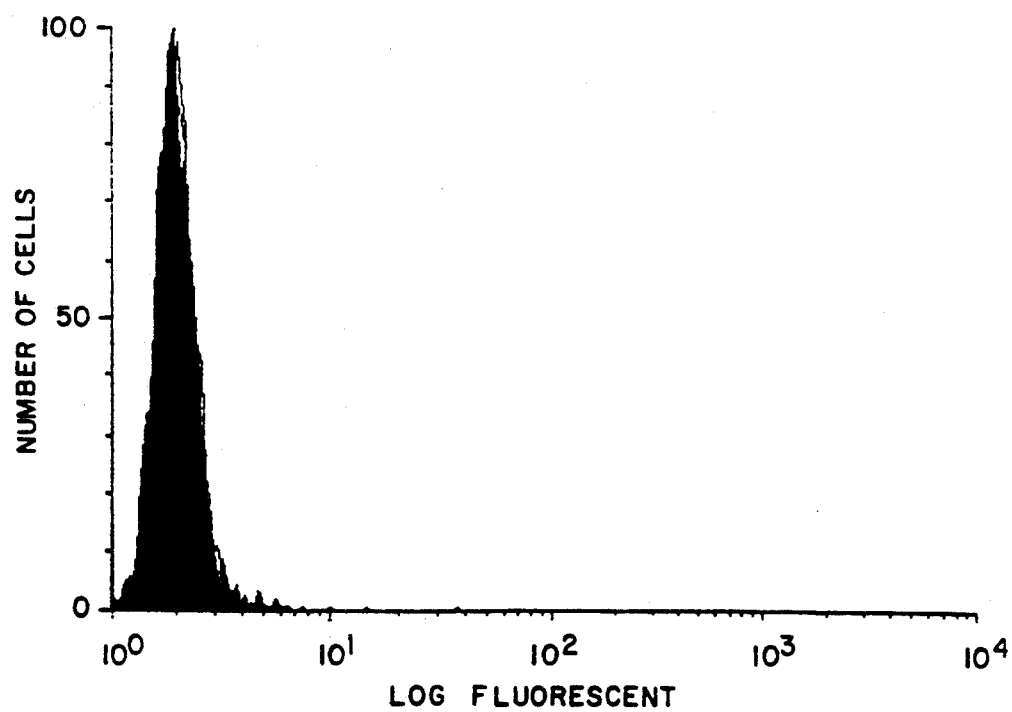
Figure 2C:
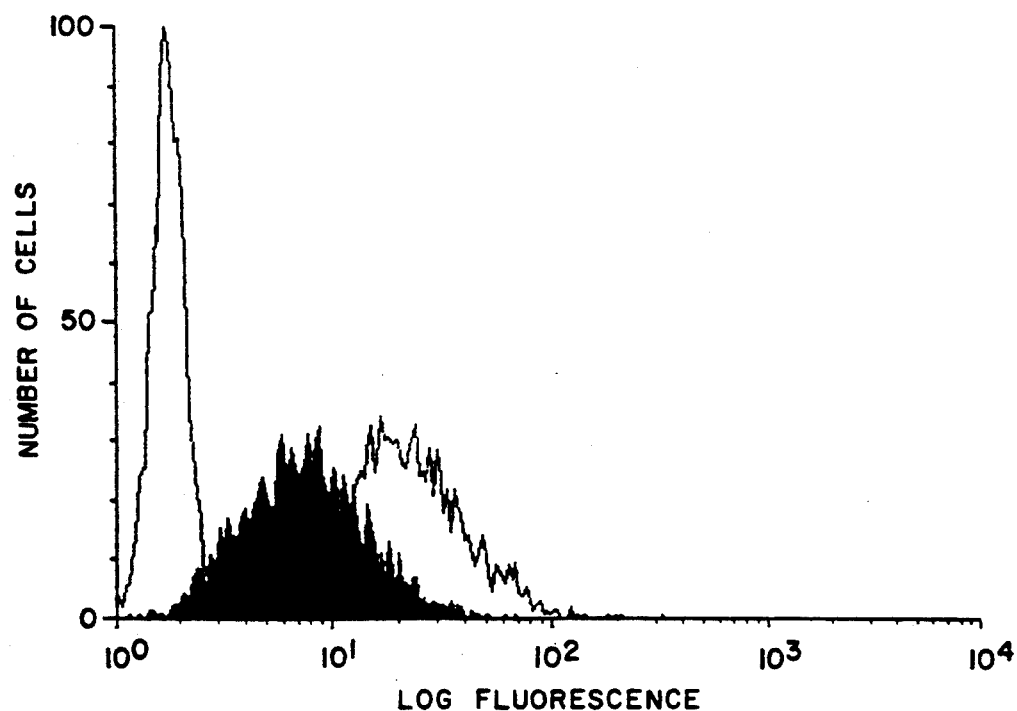
Figure 2D:
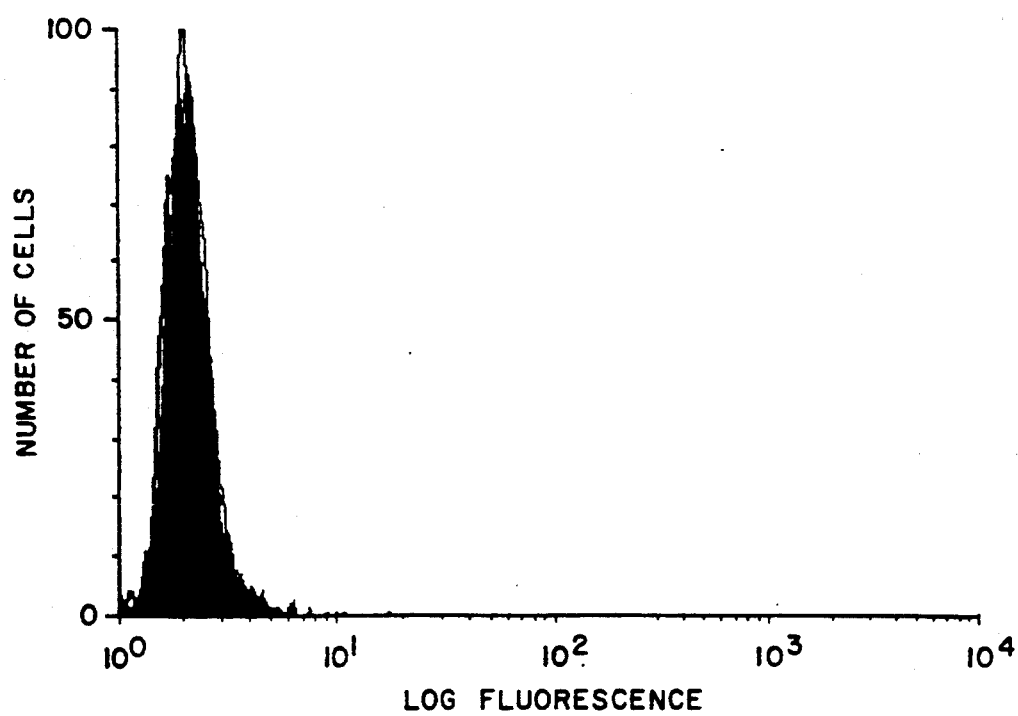
Figure 2E:
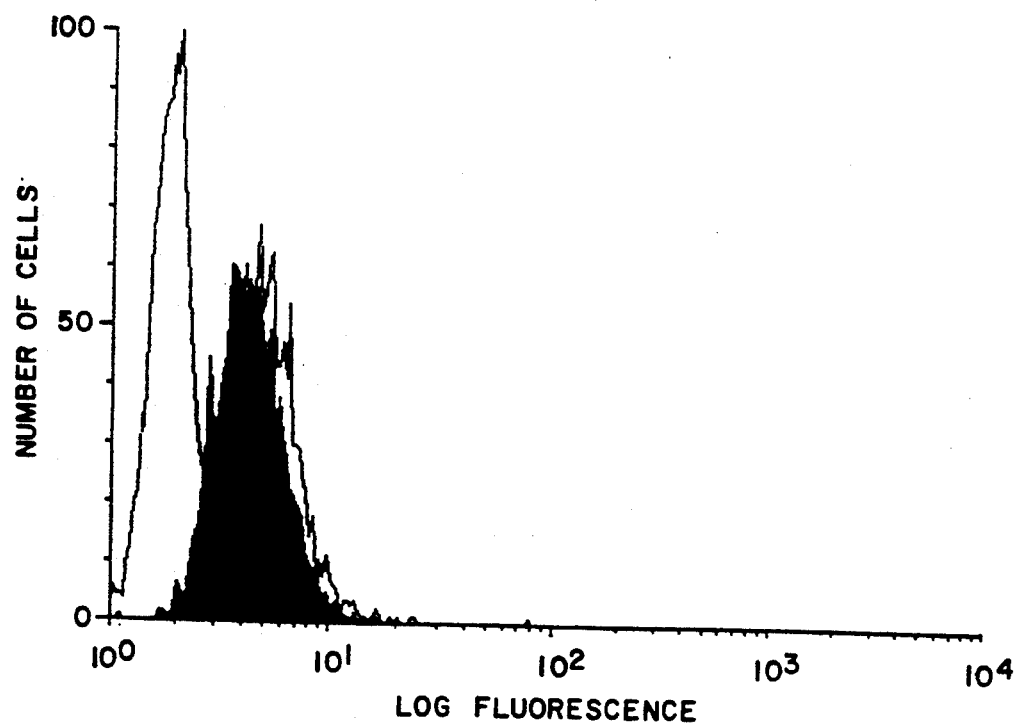
Figure 2F:
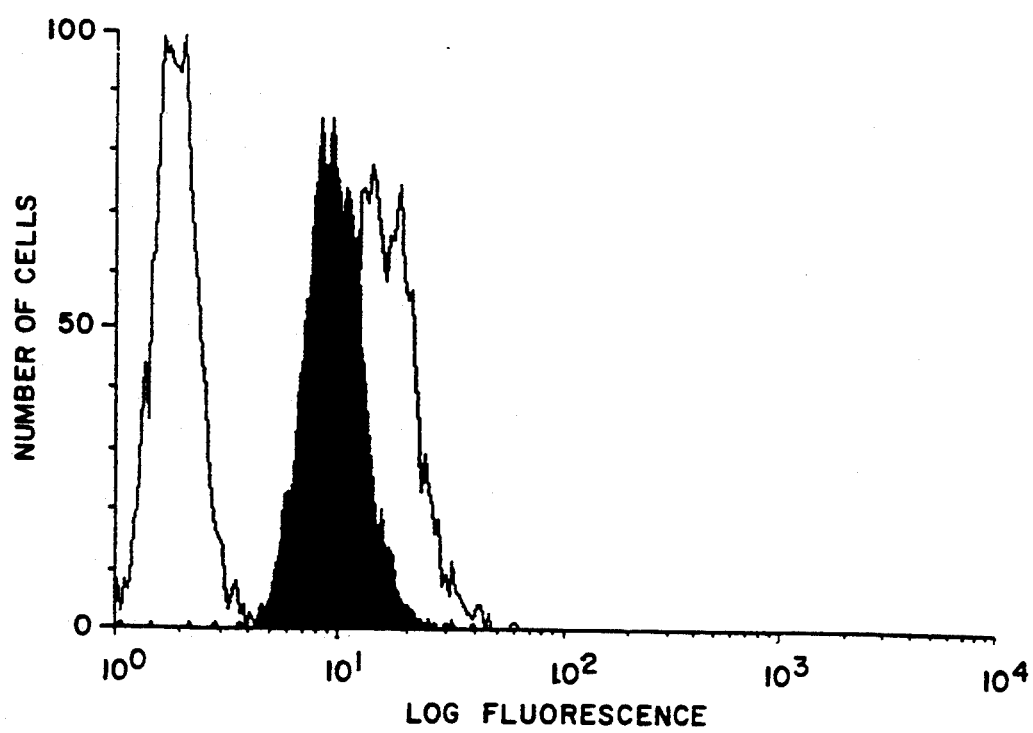
Figure 3A:
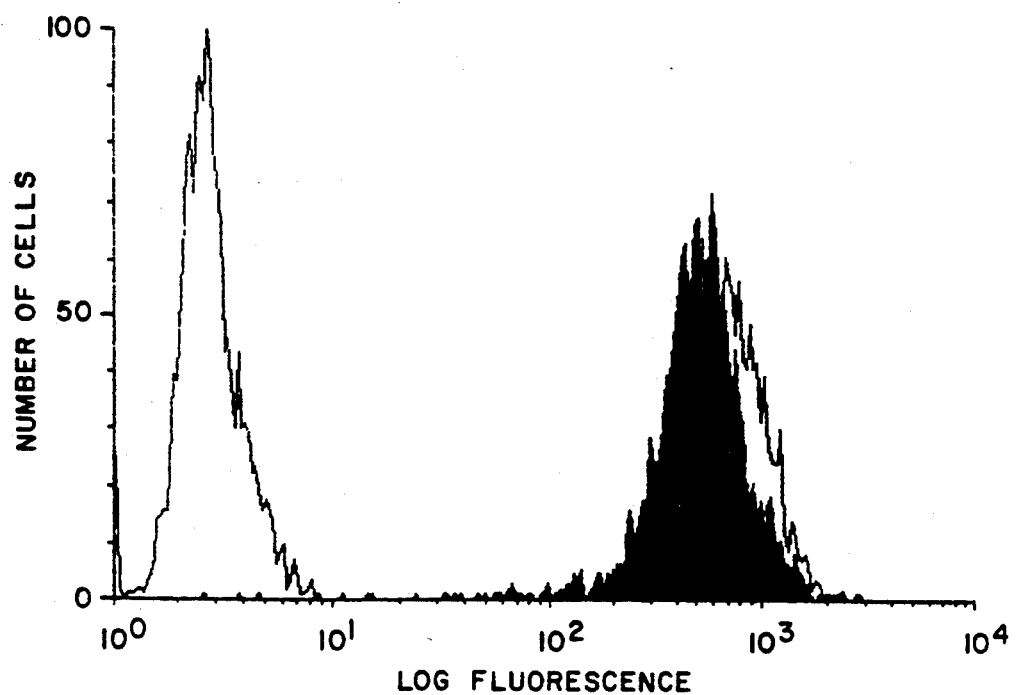
FIGS. 3A, 3B, 3C, 3D, 3E and 3F are FACS analyses demonstrating specificity of MoAb 176.4G2.
Figure 3B:
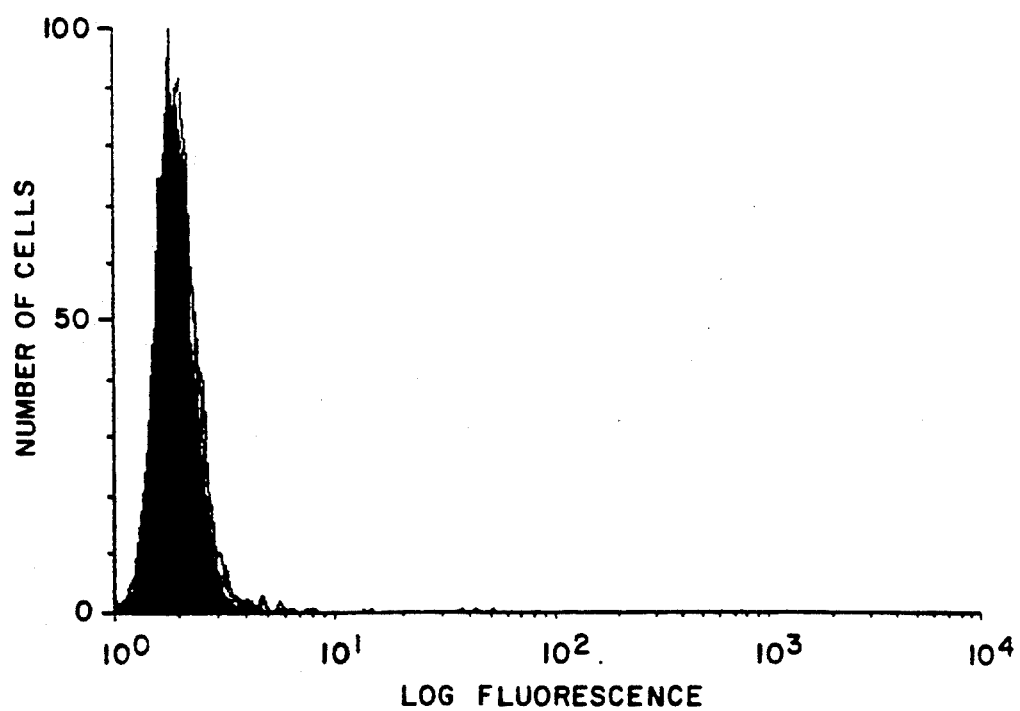
Figure 3C:
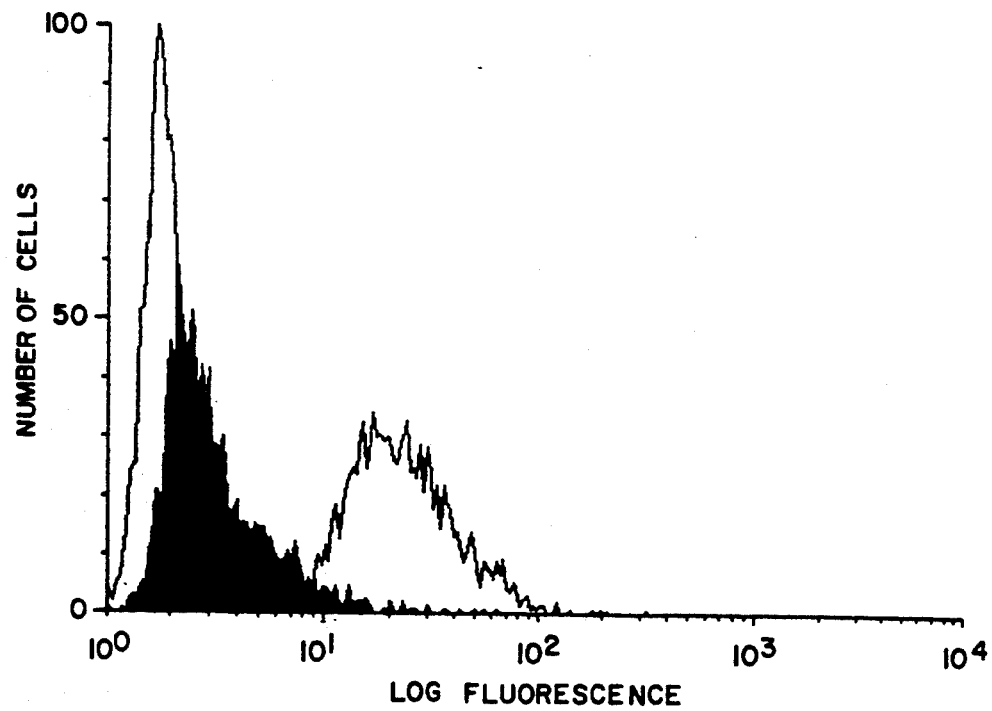
Figure 3D:
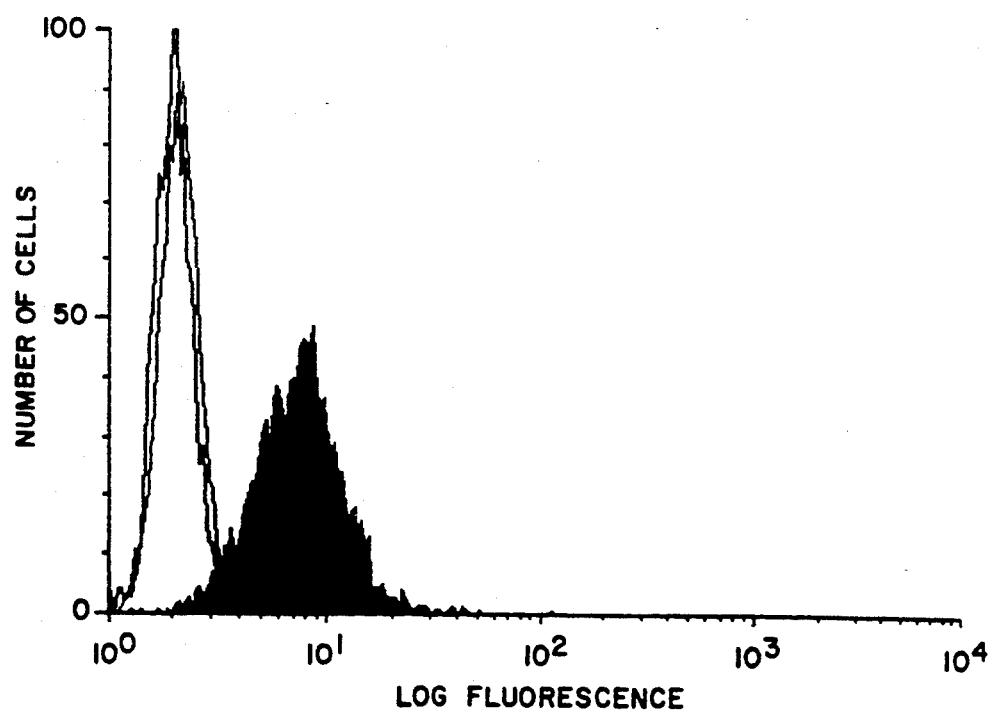
Figure 3E:
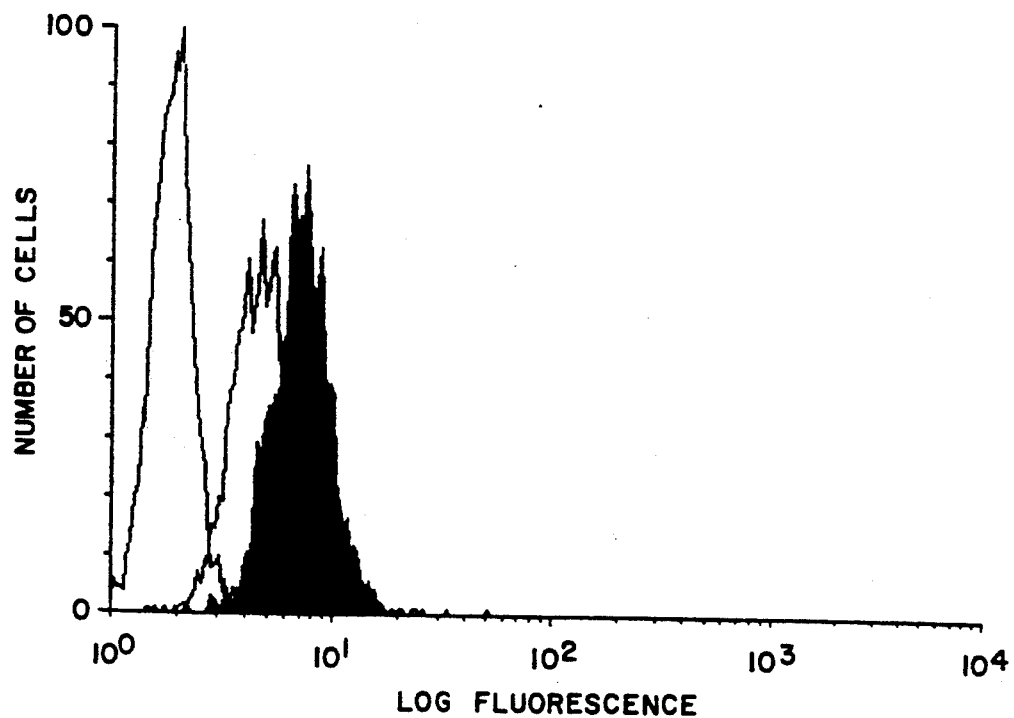
Figure 3F:
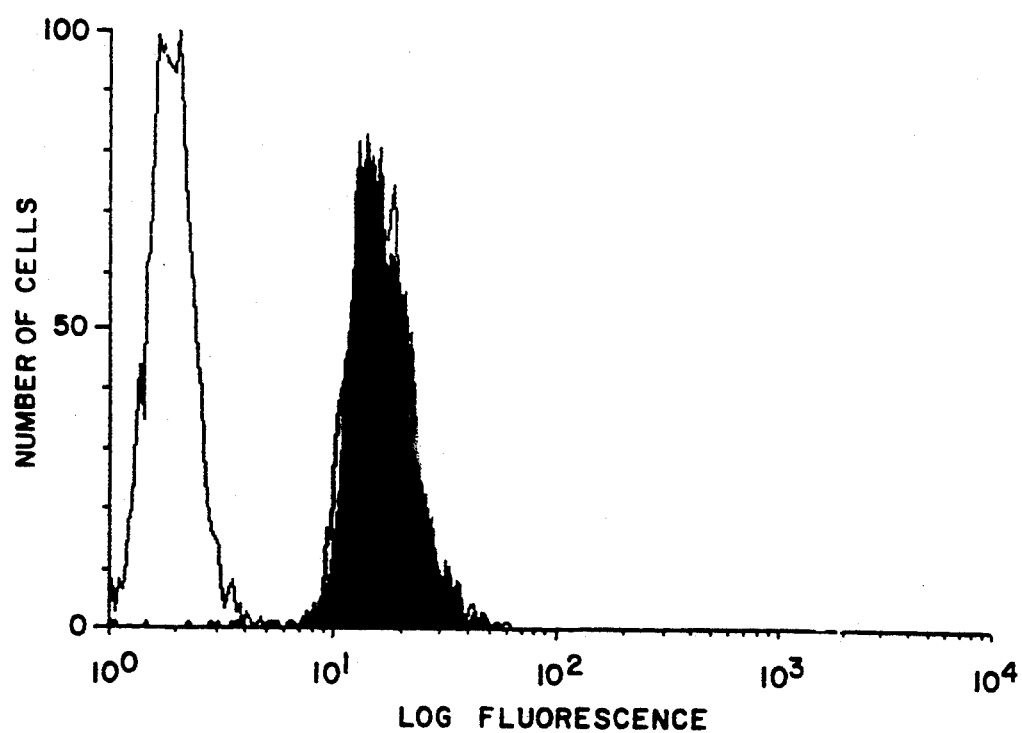

Monoclonal antibodies were assayed for binding to six (6) transfectant cell lines expressing individual CEA family member native proteins as cell surface antigens, as shown in FIGS. 1-3, panels A-F. Binding is shown by shaded histograms compared to normal serum, and positive control Ab (53.5) for each cell line.

MoAb 176.7.5A, shows specificity to TM-CEA by binding to those cell lines expressing TM-CEA (23.411, c16.6 and E 22.7), as shown in FIG. 1, panels A, E, and F. MoAb 176.3G2 shows specificity to both CEA and TM-CEA by binding to cell lines ILV7-1 2 and 23.411, C16.6, E22.7, as shown in FIG. 2, panels C and A, E, F, respectively. MoAb 176.4G2 shows specificity to TM-CEA and NCA antigens by binding to cell lines 23.411; c16.6, E22.7 and BT-20.4, as shown in FIG. 3, panels A, E, F, and D respectively. MoAb 176.4G2 exhibited a very low amount of CEA cross-reactivity at higher antibodies concentrations.

Further characterization by Western blot analysis has confirmed the specificity demonstrated by FACS analysis. Subsequent FACS and IFF experiments using MoAb 176.7.5A demonstrate recognition of native TM-CEA at the cell surface of cultured tumor cell lines, a source of specific antigen other than that expressed in a transfectant cell line.

Preparation of CEA antibodies to native protein

CEA was purified by liquid column chromatography of detergent extracts of human colon adenocarcinoma cell lines. Cell pellets were sonicated in buffer containing 1% Triton X-100 and phenylmethyl sulfonyl fluoride, benzamidine and EDTA as protease inhibitors. CEA was sequentially purified by anion exchange chromatography on Bio-Gel DEAE-5-PW column (Bio-Rad Laboratories), cation exchange chromatography on carboxymethyl cellulose (Bio-Rad Laboratories) and gel permeation chromatography on Bio-Sil TSK-400 and -250 columns (Bio-Rad Laboratories).

Mice were immunized with aqueous solutions of CEA emulsified 1:1 with Freund's complete adjuvant. Booster injections of antigen emulsified 1:1 in Freund's incomplete adjuvant were given at biweekly intervals until high serum titers of anti-CEA antibodies were detected. Spleens from such animals were removed and splenocytes were fused with murine myeloma cells, P3-X63-AG8.653, by standard fusion methods. Primary screening for anti-CEA antibodies was performed by sandwich ELISA assay using a solid-phase rabbit polyclonal trapping antibody to bind CEA and then adding hybridoma culture supernatants to detect the presence of mouse anti-CEA antibody. The binding of the mouse antibody from culture supernatants was detected by adding peroxidase-conjugated anti-mouse Ig antibodies and, following wash steps, the addition of peroxidase enzyme substrate. Production of colored product by the enzyme indicated the presence of mouse anti-CEA antibody in the hybridoma supernatant.

Production of anti-NCA antibodies using synthetic peptides

The largest contiguous string of unique amino acid sequence (when compared to CEA and TM-1 sequences) is the tetrapeptide, Ser-Lys-Ala-Asn, located at amino acid sequence position 211-214. A synthetic peptide, Pro-Ser-Lys-Ala-Asn-Tyr-Cys (residues 210-215 of the NCA sequence with Cys added for coupling purposes), was prepared using Merrifield solid phase synthetic chemistry. Since the smallest generally accepted size for peptide epitopes is about four amino acids, the Pro residue on the amino terminus and the Tyr residue on the carboxy terminus were included to block the free N- and C-termini of critical tetrapeptide immunogen. The peptide was coupled to keyhole limpet hemocya in (KLH) using the heterobifunctional coupling reagent, m-maleimidobenzoyl-N-hydroxysulfosuccinimide (sulfo-MBS). The same peptide was coupled to bovine serum albumin (BSA) using the heterobifunctional coupling reagent, N-succinimidyl 3-(2-pyridyldithio)propionate (SPDP).

Mice were immunized with emulsions of peptide-KLH (100 ug) in Freund's complete adjuvant. Boosters were given with antigen emulsions in Freund's incomplete adjuvant until anti-peptide titers rose. Splenocytes from these animals were fused to mouse myeloma cells using standard fusion techniques. Using the hexapeptide-carrier immunogen, we obtained 11 different monoclonal anti-peptide antibodies using the peptide-BSA as a solid phase screening reagent. It was subsequently found that none of these antibodies were capable of binding to either native o dentatured NCA protein. Two additional fusions gave the same results making it apparent that antibodies derived to such short peptides generally are not capable of binding to this peptide sequence in the context of the whole (denatured) protein. Since the surrounding sequence is common to NCA, CEA and TM-CEA, lengthening the peptide immunogen by inclusion of surrounding sequence runs the risk of eliciting cross-reactive antibodies. Using the same techniques multimers of the four amino acid prepared. Peptide-KLH immunogens consisted of the repeating sequence (PSKANY)$_x$-KLH where x=2–5 repeating units. The immunogen (PSKANY)$_3$-KLH yielded NCA-specific monoclonal antibodies reactive with the denatured NCA protein.

Screening Assay

A sandwich immunoassay using antibodies 176.7.5A(TM-CEA specific) and MoAb CII13.9a (cross-reactive with CEA, TM-CEA and NCA) was used to screen sera from cancer patients. Antibody 176.7.5a is labelled with Fluroscein Isothiocynate (FITC) and antibody 113.9a is conjugated to alkaline phosphatase. The two derivatized antibodies are allowed to incubate with serum to be analyzed during which time they form an antibody-antigen-antibody sandwich with any TM-CEA in the serum. After 20 minutes, magnetizable particles coated with anti-fluorescein antibody are added, the complex, washed, and detected by adding p-nitrophenyl phosphate as an enzyme substrate. Reaction rate is monitored at 405 nm. Using this method, 80–90 sera samples, from patients diagnosed as having colon, lung, breast and pancreatic cancers, were analyzed. As a control, 20–30 sera samples, from non-smoking normal individuals, were analyzed. From 15 to over 30% of sera samples from cancer patients evidenced TM-CEA levels greater than the entire pool of the control.

An additional assay used the two antibodies, monoclonal antibody 176.7.5a and rabbit polyclonal anti-CEA (DAKO Corporation). Polyclonal antibody (0.2 ugm) is absorbed in 0.1M carbonate/bicarbonate buffer, pH 9.5, to the wells of Immulon ELISA plates (Dynatech Laboratories, Inc.) for 1 hr at 37° C. The excess antibody is washed off and the wells blocked with PBS containing 0.05% Tween-20 (PBS-T) for 1 hr at 37° C. A lysate of cell line 23.411 containing TM-CEA is added in serial dilutions to the antibody-coated wells and incubated for 1 hr at ambient temperature. The wells are washed and 100 ul of antibody 176.7.5a in PBS-T is added to each well and incubated for 1 hr at ambient temperature. Unbound antibody is washed off and a goat anti-mouse IgG, A,M-peroxidase conjugate in PBS-T is added and incubated at ambient temperature for 1 hr. Antigen-dependent binding of the 176.7.5a antibody and anti-mouse-enzyme conjugate are detected after washing the wells by the addition of peroxidase enzyme substrate and monitoring the production of color.

We claim:

1. In an immunoassay method for differentiating between family members of the CEA gene family, wherein a serum or plasma sample is contacted with an antibody that specifically recognizes one or more of said family members, under conditions sufficient to allow said antibody to bind to said family member or members to form antibody-antigen products, and such antibody-antigen products are detected, the improvement which comprises employing as said antibody, a monoclonal antibody (a) which binds specifically with TM-CEA but does not crossreact with CEA or NCA, (b) which binds specifically with TM-CEA and CEA but does not crossreact with NCA, or (c) which binds specifically with TM-CEA and NCA but does not crossreact with CEA.

2. The immunoassay method of claim 1 wherein said antibody binds specifically with TM-CEA but does not crossreact with CEA or NCA.

3. The immunoassay method of claim 1 wherein said antibody binds specifically with TM-CEA and CEA but does not crossreact with NCA.

4. The immunoassay method of claim 1 wherein said antibody binds specifically with TM-CEA and NCA but does not crossreact with CEA.

5. The immunoassay method of any one of claims 1 to 4 wherein said family member is a native protein or has been subject to denaturation.

6. In an immunoassay kit for differentiating between family members of the CEA gene family, which comprises (1) a first antibody that specifically recognizes one or more of said family members, and (2) a second antibody which binds with the antibody-antigen product formed by binding between said family member or members and said antibody, one of said first and second antibodies being immobilized on a solid support and the other being labeled, the improvement which comprises employing as said first antibody, a monoclonal antibody (a) which binds specifically with TM-CEA but does not crossreact with CEA or NCA, (b) which binds specifically with TM-CEA and CEA but does not crossreact with NCA, or (c) which binds specifically with TM-CEA and NCA but does not crossreact with CEA.

7. The immunoassay kit of claim 6 wherein said first antibody binds specifically with TM-CEA but does not crossreact with CEA or NCA.

8. The immunoassay kit of claim 6 wherein said first antibody binds specifically with TM-CEA and CEA but does not crossreact with NCA.

9. The immunoassay kit of claim 6 wherein said first antibody binds specifically with TM-CEA and NCA but does not crossreact wtih CEA.

10. The immunoassay kit of any one of claims 6 to 9 which additionally comprises a denaturing agent.

11. An essentially purified hybridoma-derived monoclonal antibody which binds specifically with TM-CEA but does not crossreact with CEA or NCA.

12. An essentially purified hybridoma-derived monoclonal antibody which binds specifically with TM-CEA and CEA but does not crossreact with NCA.

13. An essentially purified hybridoma-derived monoclonal antibody which binds specifically with TM-CEA and NCA but does not crossreact with CEA.

* * * * *